United States Patent
Zhong et al.

(10) Patent No.: US 8,067,073 B2
(45) Date of Patent: Nov. 29, 2011

(54) THERMOPLASTIC MEDICAL DEVICE

(75) Inventors: Shen-Ping Zhong, Shrewsbury, MA (US); Yem Chin, Burlington, MA (US); Paul Scopton, Winchester, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1915 days.

(21) Appl. No.: 10/811,277

(22) Filed: Mar. 25, 2004

(65) Prior Publication Data

US 2005/0214492 A1 Sep. 29, 2005

(51) Int. Cl.
*B32B 1/02* (2006.01)
*B32B 1/08* (2006.01)

(52) U.S. Cl. ............... 428/35.7; 428/34.1; 428/34.2; 428/35.9; 428/36.9

(58) Field of Classification Search ........... 428/34.1, 428/34.2, 35.7, 35.9, 36.9
See application file for complete search history.

(56) References Cited

U.S. PATENT DOCUMENTS

| | | | |
|---|---|---|---|
| 3,388,095 A * | 6/1968 | Huntjens | 524/91 |
| 5,227,457 A | 7/1993 | Marrocco, III et al. | 528/183 |
| 5,247,057 A | 9/1993 | Tan et al. | 528/353 |
| 5,248,305 A | 9/1993 | Zdrahala | 604/280 |
| 5,514,379 A * | 5/1996 | Weissleder et al. | 424/426 |
| 5,731,400 A | 3/1998 | Marrocco, III et al. | 528/125 |
| 5,760,131 A | 6/1998 | Marrocco, III et al. | 525/58 |
| 5,976,437 A | 11/1999 | Marrocco, III et al. | 264/126 |
| 6,024,722 A * | 2/2000 | Rau et al. | 604/96.01 |
| 6,025,439 A | 2/2000 | Arnold et al. | 525/180 |
| 6,087,467 A | 7/2000 | Marrocco, III et al. | 528/125 |
| 6,228,285 B1 | 5/2001 | Wang et al. | 252/299.01 |
| 6,242,063 B1 | 6/2001 | Ferrera et al. | 428/35.2 |
| 6,284,333 B1 | 9/2001 | Wang et al. | 428/35.5 |
| 6,436,056 B1 | 8/2002 | Wang et al. | 600/585 |
| 6,517,570 B1 * | 2/2003 | Lau et al. | 623/1.13 |
| 6,676,971 B2 | 1/2004 | Goupil et al. | 424/489 |
| 6,730,377 B2 | 5/2004 | Wang | 428/35.7 |

FOREIGN PATENT DOCUMENTS

| | | |
|---|---|---|
| EP | 1 352 731 | 10/2003 |
| EP | 1 522 549 A1 | 4/2005 |
| WO | WO 2004.004592 A1 | 1/2004 |
| WO | WO 2004/106420 A2 | 12/2004 |

OTHER PUBLICATIONS

Mississippi Polymer Technologies, "Parmax® Applications", http://www.mptpolymers.com/applications.shtml, Sep. 4, 2003, 5 pgs.

* cited by examiner

*Primary Examiner* — Marc Patterson
(74) *Attorney, Agent, or Firm* — Seager, Tufte & Wickhem, LLC

(57) ABSTRACT

An medical device such as a guidewire or a catheter having a flexible elongate component which comprises a thermoplastic rigid rod polymer, which component may comprise a bundle of threads, a sleeve, a coil, a co-extrusion, a strut, or other suitable component.

48 Claims, 4 Drawing Sheets

THERMOPLASTIC MEDICAL DEVICE

FIELD

The present invention generally relates to medical devices. More particularly, the present invention relates to catheters comprising an improved material.

BACKGROUND

Medical devices often require a confluence of characteristics not readily achievable in a single device. For instance, in medical devices such as guidewires and catheters, the device is often navigated distally through a tortuous vascular system. This requires high levels of pushability, torqueability, and flexibility while retaining a narrow cross-sectional area. It is also desired to have a device which minimizes the trauma to the surrounding vessels. One way to minimize this trauma is through a soft distal tip. Other characteristics that are often desirable include MRI compatibility and radiopacity. There is thus an ongoing need to provide alternative structures and designs for such medical devices.

SUMMARY

One example embodiment pertains an elongated medical device having an flexible elongated element formed from a thermoplastic rigid-rod polymer such as substituted poly(1, 4-phenylene). The element may provide a significant portion of the medical devices mechanical characteristics such as torqueability, pushability, and flexibility.

Another example embodiment pertains to an a guidewire comprising a elongated member made from a thermoplastic rigid-rod polymer. The elongated member may be a core wire of the guidewire. The core wire may run from substantially the proximal portion of the guidewire to the distal portion of the guidewire. The core wire may have a generally circular cross-sectional shape or may have a rectangular or X-shaped cross-sectional shape. The guidewire may include a sheath made from the thermoplastic rigid-rod polymer or may include more than one sheath made from the thermoplastic rigid-rod polymer. The sheath may be an extruded sleeve or may be a braided sleeve. The braid may be a diamond braid or may be a crisscross braid. The guidewire may include a core having a plurality of fine threads of the polymer extending through a substantial length of the guidewire. The guidewire may have a first section having a solid core of the polymer and a second section having a plurality of fine threads of the polymer. The guidewire may have variable stiffness which may be provided by controlling the outer diameter of a polymer shaft.

Another example embodiment pertains to a catheter such as a guide catheter. The elongated member may be a sleeve made from the thermoplastic rigid-rod polymer. The sleeve may include two or more layers of the polymer. The sleeve may be braided, either in a diamond pattern or a crisscross pattern. The braided layer may be coated with another polymer and thereby impregnated with another polymer. The sleeve may also be woven. The sleeve may be a coiled polymer ribbon or may be a spring. The polymer of the sleeve may be blended or co-extruded with another polymer. The other polymer may be another thermoplastic. The blend or thickness of the layers of the coextrusion may vary along the length to provide different mechanical characteristics along desired portions.

Another example embodiment pertains to a balloon catheter such as an angioplasty or stent-delivery catheter having a balloon sleeve made from a thermoplastic rigid-rod polymer. The balloon sleeve may have a first layer that is the polymer and a second layer that is another polymer, such as a non-crosslinked nylon. The balloon may have a wall formed using variable coextrusion, with this polymer used where certain characteristics such as non-compliance are desired and another polymer where other characteristics are desired. The balloon wall may be formed from a weave or mesh of this polymer coated with or overlaying another polymer.

The above summary of some example embodiments is not intended to describe each disclosed embodiment or every implementation of the present invention. The figures and detailed description which follow more particularly exemplify these embodiments.

BRIEF DESCRIPTION OF THE DRAWINGS

The invention may be more completely understood in consideration of the following detailed description of various embodiments of the invention in connection with the accompanying drawings in which.

Figure 1:
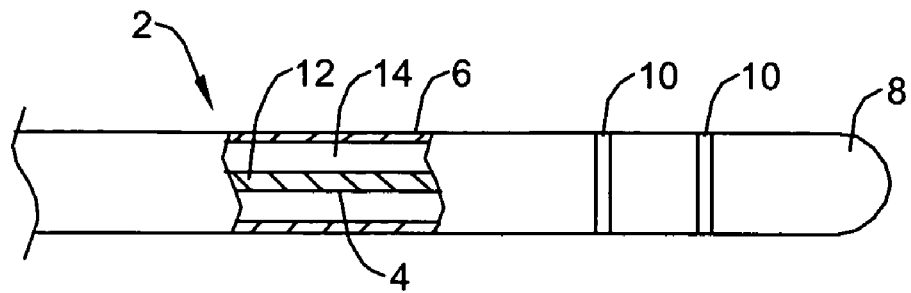
FIG. 1 depicts a diagrammatic cross-sectional view of a guidewire.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION OF EXAMPLE EMBODIMENTS

As used in this specification and the appended claims, the singular forms "a", "an", and "the" may include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

The terms torqueability, pushability and flexibility are herein defined as follows. Torqueability is the ability to transmit a rotational force from a proximal portion to a distal portion. Torqueability may be advantageous if a guidewire is shaped to conform to specific vasculature, and the guidewire needs to be specifically oriented to take full advantage of its shape. Pushability is the ability to transmit a longitudinal force from a proximal portion to a distal portion so that the longitudinal displacement of the distal portion is approximately the same as the longitudinal displacement of the proximal portion. In contrast, a device that does not exhibit a high degree of pushability would displace laterally near the proximal portion, creating bends or curves in the device. Flexibility is the ability of a device to bend without breaking or elastic deformation.

FIG. 1 is a diagrammatic cross-sectional view of a guidewire 2. Guidewire 2 includes a core member 4 and an outer lubricious sheath 6. Guidewire 2 may also include an atraumatic distal tip 8 and one or more radiopaque markers 10 or may include a radiopaque material incorporated into one or more of the materials. For example, a radiopaque material may be incorporated into core member 4 or distal tip 8. Core member 4 is preferably made from a thermoplastic rigid rod polymer. Consequently, guidewire 2 may be compatible with magnetic resonance imaging while retaining necessary torqueability, pushability and flexibility requirements. Core member 4 may have a variable cross section. For instance, it may be distally tapered, it may have tapering regions and straight regions, or it may have one or more necked region. Core member 4 may include another polymer such as polyimide, for example, in additional to the thermoplastic rigid rod polymer.

Guidewire 2 may be formed by extruding core member 4 and extruding sheath 6 over core member 4. Sheath 6 may be lubricious and may include therapeutic agents. For example, sheath 6 may include PTFE or may include a drug infused hydrogel. Alternatively, core member 4 may be formed by coextruding the thermoplastic rigid rod polymer with another compatible polymer. The coextrusion process may be controlled to extrude variable amounts of the thermoplastic rigid rod polymer and the other polymer to produce a variable stiffness core member. Of course, other embodiments are contemplated. For example, core member 4 may be formed from coextruding a first blend 12 and a second blend 14, each blend including a thermoplastic rigid rod polymer.

Figure 2:
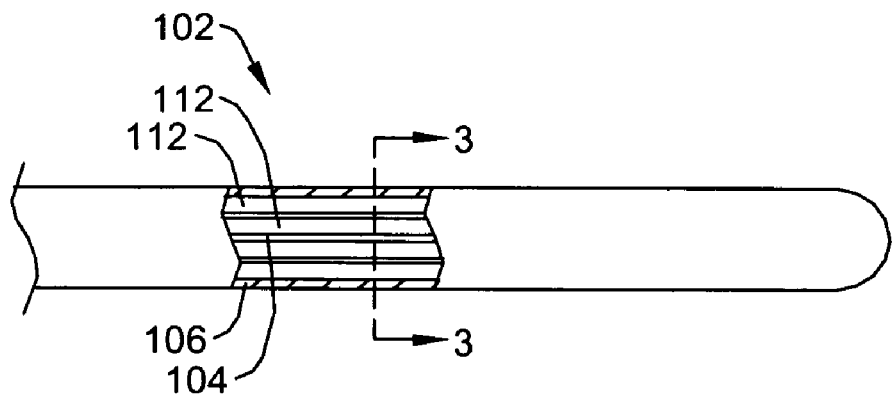
FIG. 2 depicts a diagrammatic cross-sectional view of a guidewire.
Figure 3:
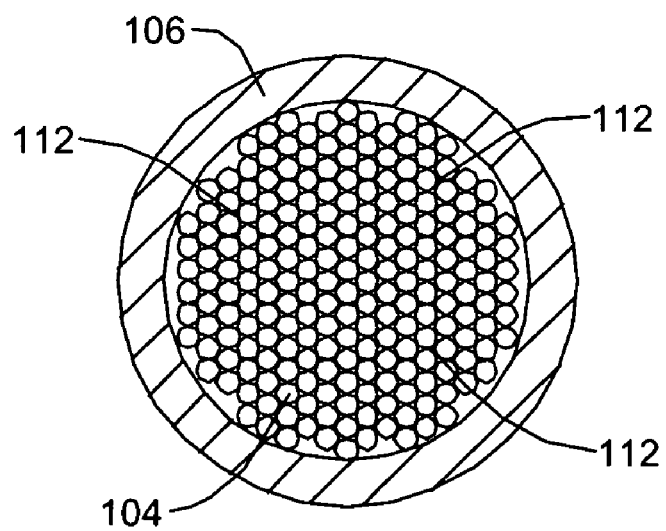
FIG. 3 depicts a lateral cross-section of the guidewire of FIG. 2.

FIG. 2 is a diagrammatic cross sectional view of an example guidewire 102. Guidewire 102 includes a core 104 formed from a plurality of elongate fibers 112, several of the fibers 112 including a thermoplastic rigid rod polymer, and may include a lubricious or polymeric sheath 106. Of course, all fibers 112 may include the thermoplastic rigid rod polymer. Alternatively, some fibers 112 may include the thermoplastic rigid rod polymer and other fibers 112 may include other polymers or materials. Some fibers 112 may vary from a first material to a second material along the length of the fiber. Fibers 112 are selected to provide for desired characteristics along the length of guidewire 102. The number and composition of fibers 112 affect the performance of guidewire 102. Generally the more fibers that include a thermoplastic rigid rod polymer, and the more of that material that is in each fiber, the fewer fibers are needed to achieve a desired level of torqueability and pushability. Other variations are contemplated as well. For instance Fibers 112 may be of variable length to permit the guidewire to taper distally. Thus, all fibers 112 would be present at a proximal portion and fewer fibers would be present distally. Alternatively, each fiber may have a tapering cross section. Variations in the cross-sectional shape are contemplated. For instance, the cross-sectional shape of certain fibers may be circular, pentagonal or square. Changing the cross-sectional shape of the fibers may change the torqueability while keeping the flexibility substantially the same, for example. Fibers 112 are retained in a sheath 106 and may be bonded at distal and proximal locations. Select fibers may also be bonded to each other or to the sheath at various other locations throughout the guidewire, which may help impart a desired shape to the guidewire. FIG. 3 is a cross-sectional view through the section lines 3-3 of FIG. 2. Guidewire 102 includes a core 104 formed from a plurality of fibers 112 encased by a sheath 106.

Figure 4:
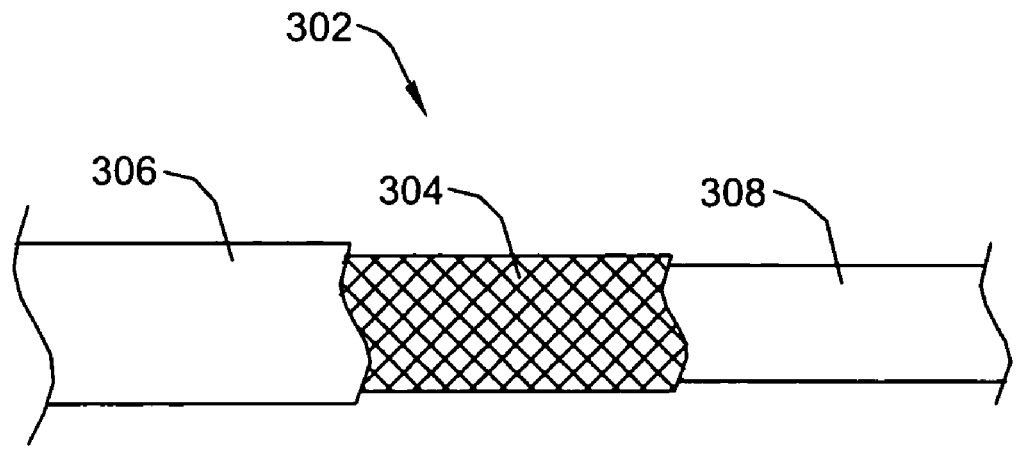
FIG. 4 depicts a partial plan view of a guide catheter.
Figure 5:
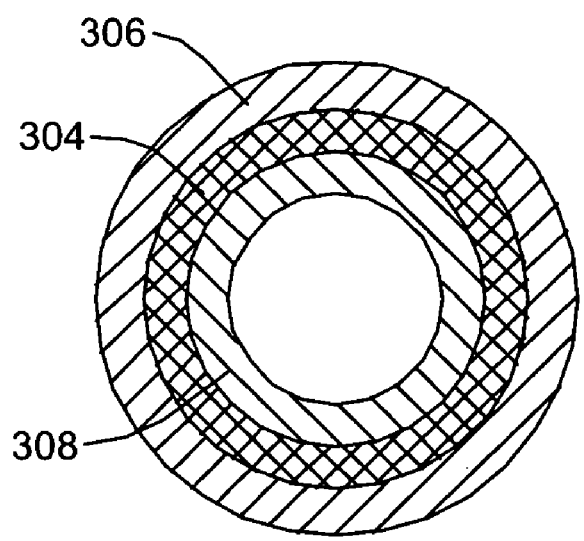
FIG. 5 depicts a lateral cross-section of the guide catheter of FIG. 4.

FIG. 4 is a partial plan view of an example guide catheter 302 with selected portions removed. FIG. 5 is a transverse cross-sectional view of the catheter of FIG. 4. Guide catheter 302 has a layer 304 including a thermoplastic rigid rod polymer and may include additional layers 306 and 308. Layer 304 may be a smooth tubular sheath or may be a weave, mesh, or coil. Layer 304 may include other polymers. For example, if layer 304 is a weave, strands made from other polymers may be woven in or the thermoplastic rigid rod weave may be imbedded in a layer having another polymer. Alternatively, the thermoplastic rigid rod polymer may be blended with other polymers. Guide catheter 302 may have a rigid rod thermoplastic layer directly bonded to a lubricious layer such as a high density polyethylene. Of course, the rigid rod thermoplastic layer may be a blended layer including one or more other polymers.

Figure 6:
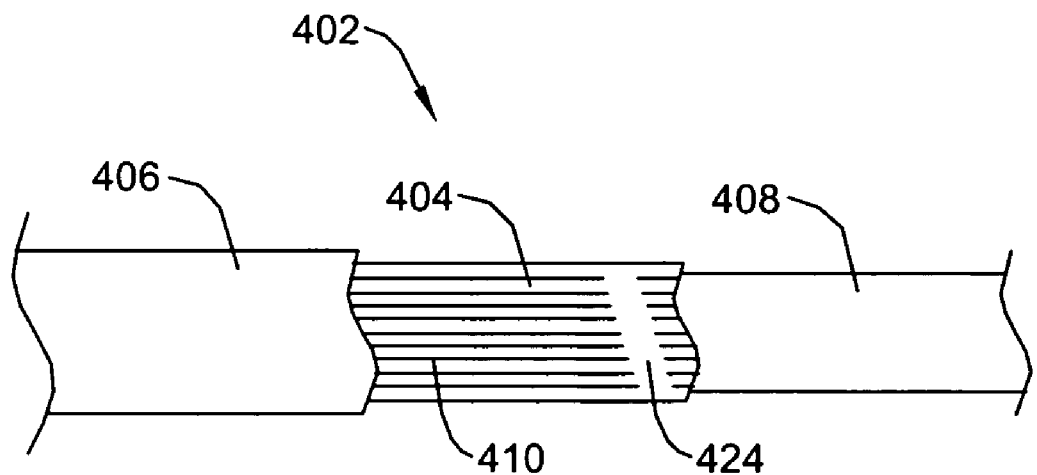
FIG. 6 depicts a partial plan view of a guide catheter.

FIG. 6 is a partial plan view of an example guide catheter 402 with selected portions removed. Guide catheter 402 has a tubular layer 404 having elongate thermoplastic rigid rod fibers 410 retained between a first tubular layer 406 and a second tubular layer 408. Fibers 410 have proximal ends 420 and distal ends 422 which may be embedded in a proximal retaining ring and a distal retaining ring. Alternatively or additionally, fibers 410 may be embedded in a retaining material 424 such as a polymer adhesive such as epoxy or polyurethane. Selected segments of fibers 410 may be embedded in a retaining material and other segments of fibers 410 may be free. This may be varied along the length of the catheter to provide desired flexibilities and shapes of the catheter. Fibers 410 may have a circular cross sectional shape, rectangular cross-section shape, or other suitable shape.

Figure 7:
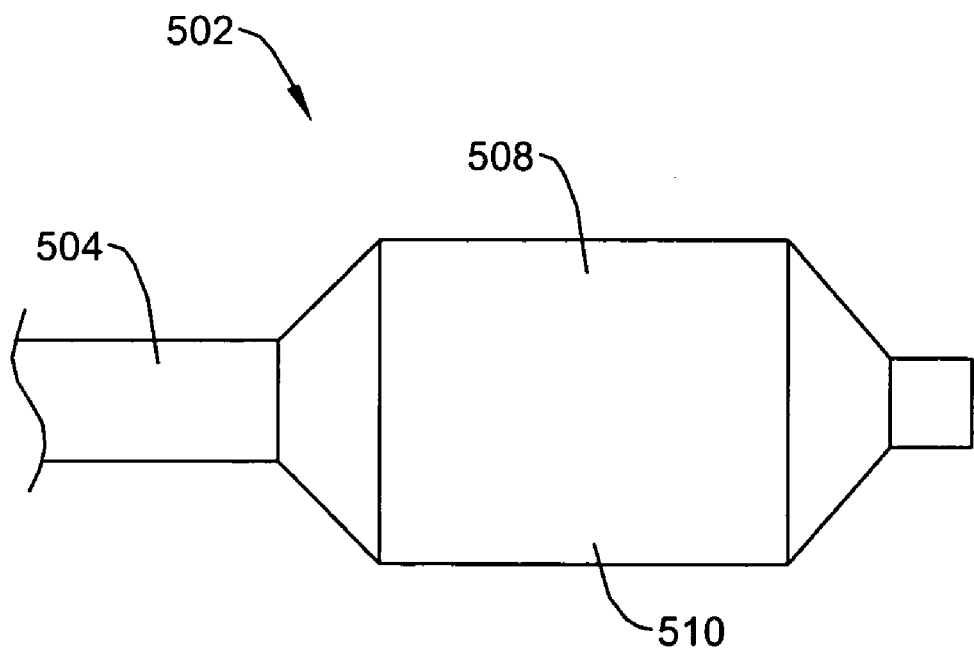
FIG. 7 depicts a partial plan view of a balloon catheter.

FIG. 7 is a partial plan view of an example balloon catheter 502. Balloon catheter 502 includes a catheter shaft 504 defining an inflation lumen fluidly connected to balloon 508 and may include a guidewire lumen. Balloon 508 includes a balloon wall 510 made from a rigid rod thermoplastic polymer, which may also be blended or coextruded with other polymers. Balloon wall may have a thickness of between 0.25 and 5.0 mils or between 0.3 and 1.0 mils while retaining sufficient burst strength to do a typical angioplasty or stent procedure. Balloon wall 510 may include a rigid rod thermoplastic polymer mesh or weave embedded in another polymer such as Nylon. The other polymer may be non-cross linked or it may be cross-linked, depending on the desired properties.

Figure 8:
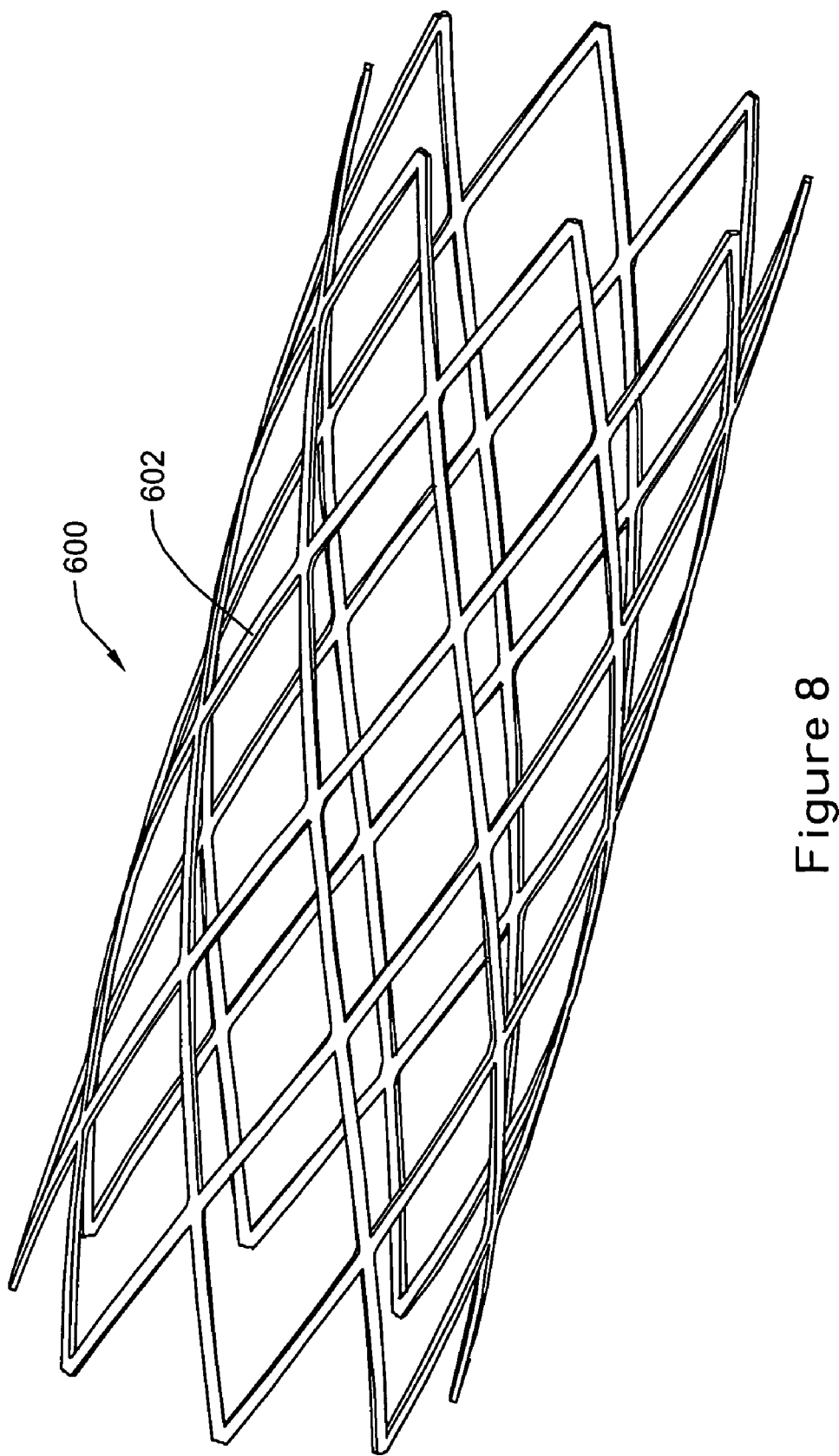
FIG. 8 depicts a perspective view of a stent.

FIG. 8 is a perspective view of an example stent 600. Stent 600 includes one or more struts 602 made from a rigid rod thermoplastic polymer arranged in a lattice-work configuration. Other suitable arrangements are contemplated. Stent 600 may include a coating which provides enhanced lubricity, carries a therapeutic agent, or provides other desired functionality. Stent 600 may also include radiopaque or paramagnetic materials to provide enhanced visibility. Stent 600 may be primarily polymeric, being made substantially from the rigid rod thermoplastic polymer, and consequently may be MRI compatible. Stent 600 may be made through compression molding or through laser cutting a tubular extrusion into the desired configuration, or through other suitable method.

Any of the medical devices described herein may be provided with a coating on a surface of the device. Such coatings may be provided for various purposes including, but not limited to, carrying a therapeutic agent for localized delivery to a target area within the body; providing a lubricious surface to facilitate introduction of the medical device into the patient during an interventional procedure; improving the biocompatibility of the medical device with the surrounding environment; or, for a combination of such or other purposes. Among coatings that have been proposed for implantable or insertable medical devices are polymeric materials such as hydrogels.

Hydrogels are typically hydrophilic polymeric materials that have the ability to absorb large amounts, up to many times the weight of the hydrogel itself, of water or other polar molecules. Hydrogels have been disclosed as coatings for implantable or insertable medical devices or as materials for constructing the device itself in, for example, U.S. Pat. Nos. 6,316,522; 6,261,630; 6,184,266; 6,176,849; 6,096,108; 6,060,534; 5,702,754; 5,693,034; and, 5,304,121, each of which is assigned to Boston Scientific Corporation or SciMed Life Systems, Inc. and is incorporated herein in its entirety by reference. Hydrogels, such as those described in the foregoing exemplary U.S. patents, can be based on synthetic or naturally occurring materials, or a composite thereof; can be biodegradable or substantially non-biodegradable; and, can be modified or derivatized in numerous ways to render the hydrogel more suitable for a desired purpose. For example, the hydrogel can be modified by chemically cross-linking with, for example, a polyfunctional cross-linking agent that is reactive with functional groups covalently bonded to the polymer structure. The hydrogel polymer can also be ionically cross-linked with, for example, polyvalent metal ions. Many hydrogel polymers mentioned herein can be both chemically and ionically cross-linked. Therefore, chemically and ionically cross-linkable hydrogel polymers are not necessarily mutually exclusive groups of hydrogel polymers.

Cross-linking of a hydrogel polymer can be advantageous, for example, to provide a more rigid material. Cross-linking may also be conducted, for example, to render the hydrogel less soluble in a particular environment or to modify the ability of the hydrogel polymer to absorb water or to modify the manner in which water or other molecules, compounds or groups are associated with the hydrogel polymer Examples of hydrogel polymers that can be adapted to render a medical device lubricious surface, without limitation, polyacrylates; poly(acrylic acid); poly(methacrylic acid); polyacrylamides; poly(N-alkylacrylamides); polyalkylene oxides; poly(ethylene oxide); poly(propylene) oxide; poly(vinyl alcohol); polyvinyl aromatics; poly(vinylpyrrolidone); poly(ethyleneimine); polyethylene amine; polyacrylonitrile; polyvinyl sulfonic acid; polyamides; poly(L-lysine); hydrophilic polyurethanes; maleic anhydride polymers; proteins; collagen; cellulosic polymers; methyl cellulose; carboxymethyl cellulose; dextran; carboxymethyl dextran; modified dextran; alginates; alginic acid; pectinic acid; hyaluronic acid; chitin; pullulan; gelatin; gellan; xanthan; carboxymethyl starch; chondroitin sulfate; guar; starch; and copolymers, mixtures and derivatives thereof.

Paramagnetic materials such as paramagnetic ions and paramagnetic particles may be incorporated into a medical device such as those described above. The paramagnetic materials may be incorporated into one or more of the polymers of the medical device. Paramagnetic materials are typically those that have a strong magnetic moment relative to detectable protons in water or other molecules, compounds or groups in the vicinity of the paramagnetic materials. Elements with atomic numbers 21-29, 42, 44, and 58-70, such as chromium (III), manganese (II), iron (III), iron (II), cobalt (II), copper (II), nickel (II), praesodymium (III), neodymium (III), samarium (III), ytterbium (III), gadolinium (III), terbium (III), dysprosium (III), holmium (III) and erbium (III) are examples of paramagnetic elements that may be suitable. The addition of paramagnetic materials may enhance MRI visualization of the medical device, for example.

A thermoplastic rigid rod polymer is a meltable polymer having constitutional or configurational units that form a generally linear chain that is rigid. Thermoplastic rigid rod polymers therefore may have increased strength compared with other thermoplastics. Thermoplastic rigid rod polymers may also have improved processing characteristics and good compatibility with other polymers compared with other polymers of similar strength. Thermoplastic rigid rod polymers may be cross-linked by cooling down from an extrusion process. Most other polymers require a radiation or chemical process to cross-link. Thus, a medical device made from a thermoplastic rigid rod polymer in combination with another polymer may have a cross-linked portion, which may increase strength, and a non-cross-linked portion, which may increase softness, flexibility or other suitable attribute. Therefore a device incorporating a thermoplastic rigid rod polymer may provide a combination of physical properties not available with a different polymer. In some embodiments, the thermoplastic rigid rod polymer may be substituted poly(1,4-phenylene). In some embodiments, the substituted poly(1,4-phenylene) includes a plurality of benzoyl substituted 1,4-phenylene units. Some of these polymers may be available commercially under the PARMAX name from Mississippi Polymer Technologies.

It should be understood that this disclosure is, in many respects, only illustrative. Numerous advantages of the invention covered by this document have been set forth in the foregoing description. Changes may be made in details, particularly in matters of shape, size and arrangement of parts without exceeding the scope of the invention. Those of skill in the art will readily appreciate that other embodiments may be made and used which fall within the scope of the claims attached hereto. The invention's scope is, of course, defined in the language in which the appended claims are expressed.

What is claimed is:

1. A medical device comprising an elongate flexible element made from a first polymer which is a substituted poly(1,4-phenylene).

2. A medical device comprising an elongate flexible element made from a first polymer which is a substituted poly(1,4-phenylene) including a plurality of benzoyl substituted 1,4-phenylene units.

3. The medical device of claim 1, wherein the medical device is an intravascular guidewire.

4. The medical device of claim 3, wherein the elongate flexible element is a core wire.

5. The medical device of claim 4, wherein the core wire extends from a position proximate the proximal end of the guidewire to a position proximate the distal end of the guidewire.

6. The medical device of claim 4, wherein the core wire comprises a plurality of elongate longitudinally extending threads made from the polymer.

7. The medical device of claim 4, wherein a substantial length of the core wire has a circular cross sectional shape.

8. The medical device of claim 4, wherein a substantial length of the core wire has a rectangular cross sectional shape.

9. The medical device of claim 4, wherein a substantial length of the core wire has a cruciate cross sectional shape.

10. The medical device of claim 4, wherein the elongate flexible element is a sleeve extending over the core wire.

11. The medical device of claim 10, further comprising a second sleeve disposed on the first, the second sleeve made from the polymer.

12. The medical device of claim 10, wherein the sleeve is an extruded tube.

13. The medical device of claim 10, wherein the sleeve is a coil.

14. The medical device of claim 13, wherein the sleeve is formed from a wound flat tape.

15. The medical device of claim 10, wherein the sleeve is a mesh.

16. The medical device of claim 10, wherein the sleeve is a weave.

17. The medical device of claim 1, wherein the medical device is a catheter.

18. The medical device of claim 17, wherein the flexible elongate element is a sleeve.

19. The medical device of claim 18, further comprising a second sleeve disposed on the first, the second sleeve made from the polymer.

20. The medical device of claim 18, wherein the sleeve is an extruded tube.

21. The medical device of claim 18, wherein the sleeve is a coil.

22. The medical device of claim 21, wherein the sleeve is formed from a wound flat tape.

23. The medical device of claim 18, wherein the sleeve is a mesh.

24. The medical device of claim 18, wherein the sleeve is a weave.

25. The medical device of claim 18, further comprising an inner sleeve and an outer sleeve, the flexible elongate element comprising a plurality of elongate threads disposed between the inner sleeve and the outer sleeve.

26. The medical device of claim 1, wherein the elongate flexible element comprises a blend of the first polymer and a second polymer.

27. The medical device of claim 1, wherein the medical device comprises a second polymer, wherein the first polymer is not cross-linked and the second polymer is cross-linked.

28. The medical device of claim 1, wherein the medical device comprises a balloon.

29. The medical device of claim 28, wherein the elongate flexible element is a balloon sleeve.

30. The medical device of claim 29, wherein the balloon sleeve comprises a second polymer.

31. The medical device of claim 30, wherein the first polymer and the second polymer are blended.

32. The medical device of claim 30, wherein the first polymer and the second polymer are coextruded.

33. The medical device of claim 30, wherein the first polymer is in a first layer and the second polymer is in a second layer.

34. The medical device of claim 33, wherein the first layer has a distal varying thickness to create a first region having a first compliance and a second region having a second compliance less than the first compliance.

35. The medical device of claim 30, wherein the first polymer comprises a mesh or weave disposed in a layer comprising the second polymer.

36. The medical device of claim 30, wherein the first polymer is not cross-linked and the second polymer is cross-linked.

37. The medical device of claim 29, wherein the medical device is an intravascular balloon catheter and the balloon sleeve has a thickness of 0.25 to 5.0 mil.

38. The medical device of claim 37, wherein the balloon sleeve has a thickness of 0.3 to 1.0 mil.

39. The medical device of claim 1, wherein the elongate member comprises a plurality of struts forming a stent.

40. The medical device of claim 39, wherein the stent is a self-expanding stent.

41. The medical device of claim 39, wherein the stent further comprises a hydrogel coating.

42. The medical device of claim 41, wherein the hydrogel coating includes a therapeutic agent.

43. The medical device of claim 1, wherein the elongate member comprises a paramagnetic materials.

44. The medical device of claim 43, wherein the paramagnetic material is gadolinium (III).

45. The medical device of claim 1, further comprising a lubricous sheath disposed around the elongate member.

46. The medical device of claim 44, wherein the lubricious sheath comprises a hydrogel polymer.

47. A medical device comprising a flexible elongate element, the flexible elongate element formed by the process comprising the steps of:
   providing a first polymer comprising a thermoplastic rigid rod polymer;
   providing a second polymer compatible with the first polymer;
   co-extruding the first polymer with the second polymer; and
   not cross-linking the first polymer while cross-linking the second polymer.

48. A medical device comprising a flexible elongate element, the flexible elongate element formed by the process comprising the steps of:
   providing a first polymer comprising a thermoplastic rigid rod polymer;
   providing a second polymer compatible with the first polymer;
   co-extruding the first polymer with the second polymer; and
   cross-linking both the first polymer and the second polymer.

* * * * *